United States Patent [19]

Vernon et al.

[11] Patent Number: 5,021,738

[45] Date of Patent: Jun. 4, 1991

[54] FIELD VARIABLE, ELECTRONICALLY CONTROLLED, NESTED COIL EDDY CURRENT PROBE

[75] Inventors: Susan N. Vernon, Annandale, Va.; Brian Sircus; Paul M. Gammell, both of Silver Spring, Md.

[73] Assignee: The United States of America as represented by the Secretary of the Navy, Washington, D.C.

[21] Appl. No.: 498,883

[22] Filed: Mar. 26, 1990

[51] Int. Cl.⁵ .................... G01N 27/72; G01N 27/82; G01R 33/12
[52] U.S. Cl. ................................. 324/232; 324/234; 324/238; 324/242
[58] Field of Search ............... 324/226, 227, 234, 236, 324/237, 238, 239, 240, 241, 242, 243, 232; 336/170, 171, 211

[56] References Cited

U.S. PATENT DOCUMENTS

| | | | |
|---|---|---|---|
| 4,107,605 | 8/1978 | Hudgell | 324/220 |
| 4,620,152 | 10/1986 | Bains, Jr. | 324/225 |
| 4,639,669 | 1/1987 | Howard et al. | 324/239 |
| 4,719,422 | 1/1988 | deWalle et al. | 324/238 |
| 4,745,809 | 5/1988 | Collins et al. | 73/661 |
| 4,747,310 | 5/1988 | Collins et al. | 73/661 |
| 4,855,677 | 8/1989 | Clark, Jr. et al. | 324/238 |

Primary Examiner—Walter E. Snow
Attorney, Agent, or Firm—John D. Lewis; Kenneth E. Walden

[57] ABSTRACT

A compound eddy current probe comprising a nest of concentric ferrite cup core probes. Both the inner and outer radii of the activated coil can be selectively altered by operator or automatic program to correspond with the size and thickness of the material under test.

6 Claims, 5 Drawing Sheets

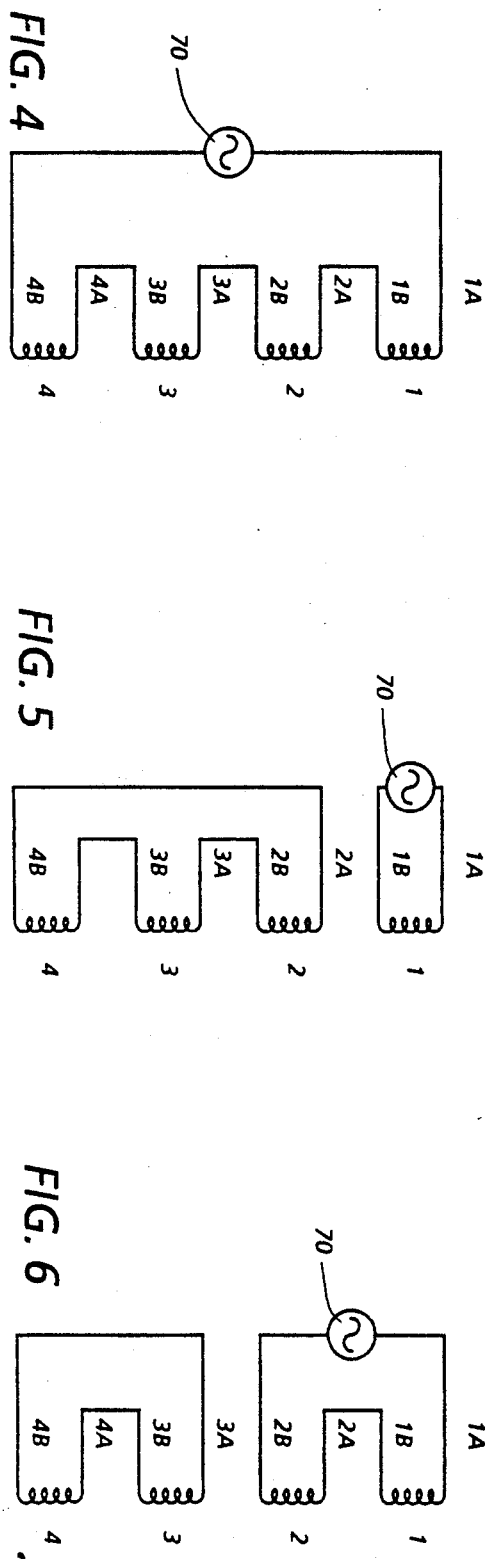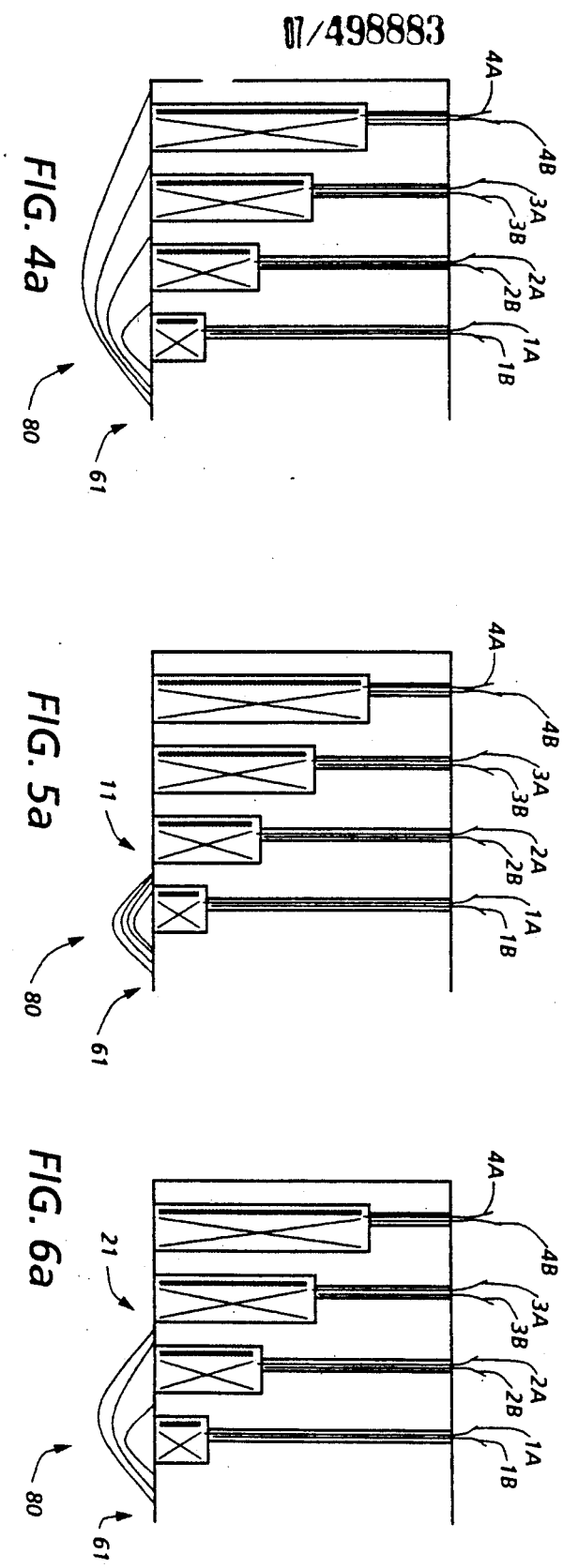

FIELD VARIABLE, ELECTRONICALLY CONTROLLED, NESTED COIL EDDY CURRENT PROBE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates to the field of eddy current testing of materials. In particular, this invention is a single nest of eddy current probes which allow the inspector to test various sizes and types of materials without changing the eddy current probe.

The nondestructive, through-thickness inspection of components by eddy current methods requires that the eddy current skin depth be on the order of the thickness of the component. The ability to identify the source of an eddy current response (defect, thickness change, lift-off change, or conductivity change), also requires that the effective radius of the probe be equal to or greater than the skin depth.

In many applications, eddy current testers and testing methods require the use of ferrite cup core probes. These ferrite cup core probes are of various sizes and generally the radius of the cup core should vary with the thickness of the material under test. Vernon, et al., Ser. No. 294,621 filed Jan. 9, 1989 teaches an "Eddy Current Method to Measure Distance Between a Scanned Surface and a Subsurface Defect" which requires the operator to choose a ferrite cup core probe having a radius roughly 1.4 times the thickness of the material under test. In this application the radius is taken to be ⅓ the outside diameter of the ferrite core. Without controlling the radius of the probe, the distance between the scanned surface and a subsurface defect cannot be determined for arbitrary thicknesses.

Another prior art method for measuring electrical resistivity entitled "Eddy Current Method for Measuring Electrical Resistivity and Device for Providing Accurate Phase Selection", Vernon, et al., Ser. No. 294,622, filed Jan. 9, 1989 also requires the operator to select a probe having a radius which varies according to the thickness of the material to be tested. Measurement of defect depth in the absence of calibration standards also requires this range of probe size to skin depth. Consequently, when a set of components having different thicknesses are to be inspected or a single component has sections of different thicknesses (i.e., aircraft wing skins) the eddy current skin depth must be changed by changing the frequency; it is also necessary to physically replace one probe with one of a different size to maintain the optimum ratio of effective radius to skin depth.

Therefore, it is an object of this invention to eliminate the need to change probes during the testing operation.

It is a further object to teach a compound probe whereby the operator can change the effective radius by simply selecting a switch, or switches.

It is still another object to teach a device that is adaptable to software control, thus reducing the required operator training.

It is a further object of the instant invention to teach a single nested eddy current ferrite cup core probe capable of exhibiting a number of discrete probe radii.

These and other objects and advantages are provided by the present invention by teaching a compound multi-diameter probe consisting of concentric nests of ferrite cup core probes which can be individually activated either by operator action or software control.

Other objects, advantages and novel features of the present invention will become apparent from the following detailed description of the invention when considered in conjunction with the accompanying drawings.

BRIEF DESCRIPTION OF THE DRAWINGS

FIG. 4 is a wiring diagram showing the electrical connection of the coils of the device of FIG. 2 wherein the probe is operating at maximum radius.

FIG. 4a depicts the flux lines associated with the hookup illustrated in FIG. 4.

FIG. 5 is a wiring diagram showing the electrical connection of the coils of the device of FIG. 2 wherein the probe is operating at minimum radius.

FIG. 5a depicts the flux lines associated with the hookup illustrated in FIG. 5.

FIG. 6 is a wiring diagram showing the electrical connection of the coils of the device of FIG. 2 wherein the probe is operating at the next to smallest radius.

FIG. 6a depicts the flux lines associated with the hookup illustrated in FIG. 6.

DETAILED DESCRIPTION OF THE INVENTION

Figure 1:
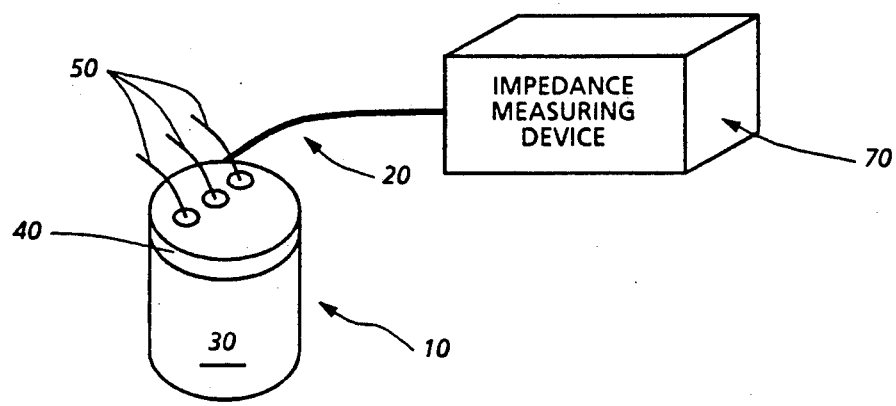
FIG. 1 is a pictorial of the invention shown connected to an eddy current system.
Figure 1A:
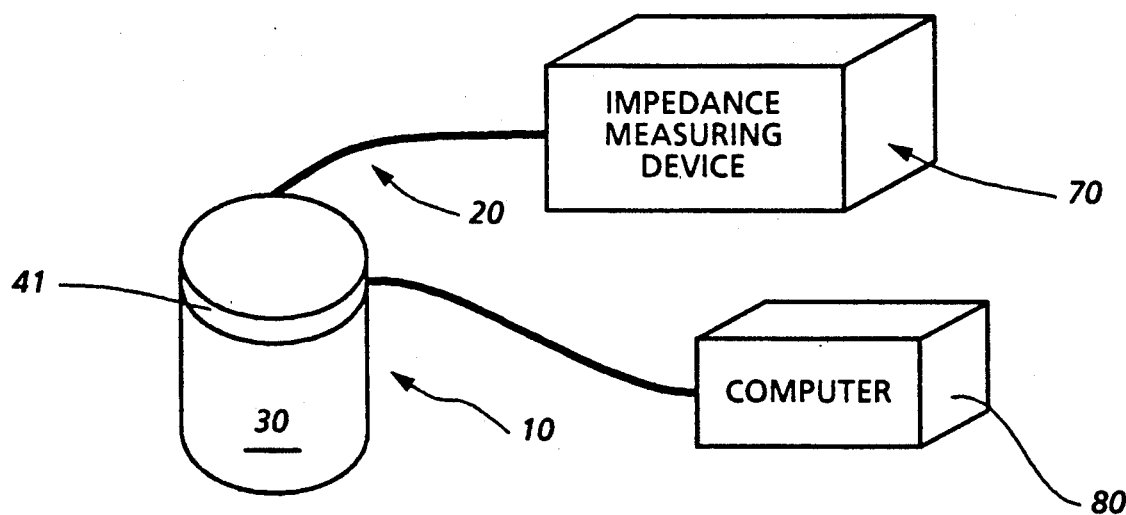
FIG. 1a is an illustration of an embodiment of the invention of FIG. 1 wherein the invention is computer controlled.

Turning now to FIG. 1, an impedance measuring device 70 is illustrated in electrical connection via wiring 20, to the selectable compound probe of the present invention 10. Therein a probe housing 30 contains a nested series of eddy current coils (not shown), which are selected by switching means 40. Switching means 40 may contain a set of operator controlled mechanical switches 50. Any means of selectively engaging the different nested coils will work, however, including computer controlled electronic switches. FIG. 1a illustrates an embodiment of the invention wherein a computer controlled switching unit 41 is controlled by a computer 80. Switching module 40 is illustrated in FIG. 1 with 3 mechanical toggle switches for simplicity. In the preferred embodiment, many more mechanical toggles were used and any switching arrangement that selectively engages and isolates the various coils is considered within the scope of this invention.

Figure 2:
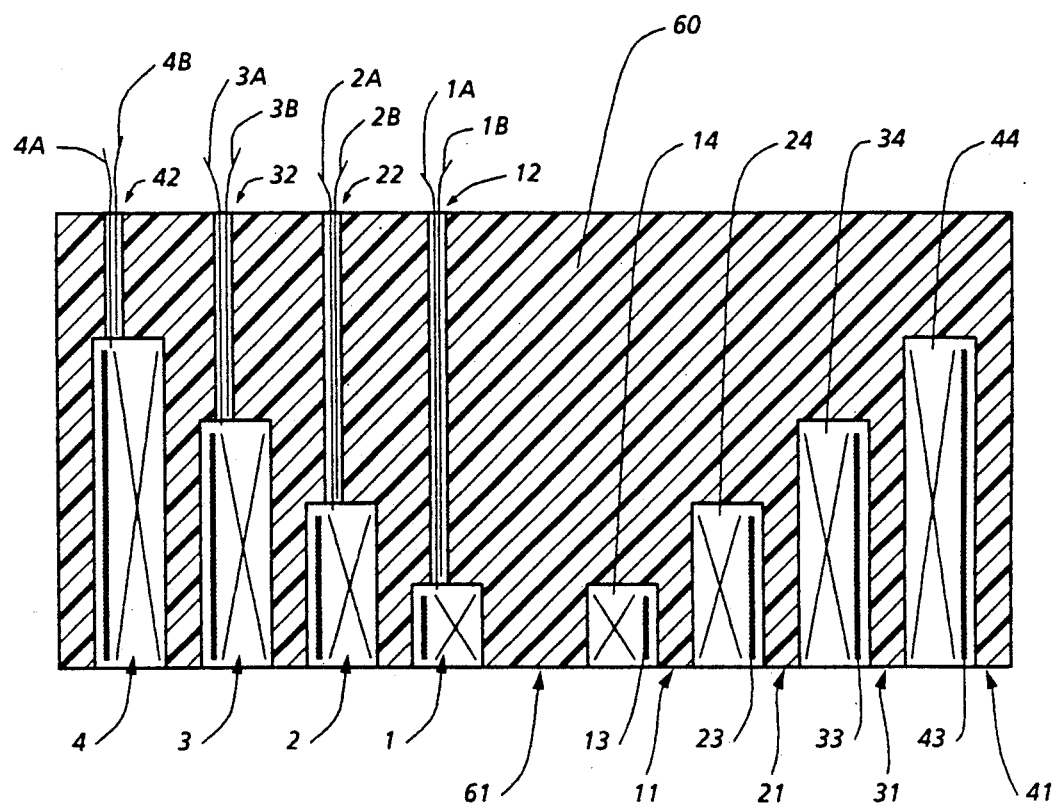
FIG. 2 is a cross-sectional illustration of one embodiment of the compound probe having four concentric ferrite cup core probes.

FIG. 2 illustrates one embodiment of the compound multi-diameter ferrite cup core probe without illustrating the housing 30 or switching means 40 shown in FIG. 1. The probe consists of a concentric nest of individually selected probe coils. FIG. 2 is a cross-section of an embodiment having 4 separate and selectively distinct probe radii. Therein a block of ferrite material 60 has grooves or channels 14, 24, 34 and 44 machined into one of its flat surfaces. The center of the block becomes a center post 61 of ferrite material 60 which forms the inner surface of the cup of the probe(s). The outer surface of this smallest radius cup core probe is formed by a circle or ring of ferrite material 11 which also is the inner surface of the next largest radii ferrite cup core probe. Within each of the machined channels 14, 24, 34 and 44 are coils, numbered 1, 2, 3, and 4, nested within the channels. Machined through the bottom of each channel 14, 24, 34 and 44 are electrical access holes 12, 22, 32, and 42 which allow electrical leads 1A-1B, 2A-2B, 3A-3B and 4A-4B to connect the electrical coils 1, 2, 3 and 4 with a switching mechanism (not shown in FIG. 2) which then connects to the eddy current instrument.

Figure 3:
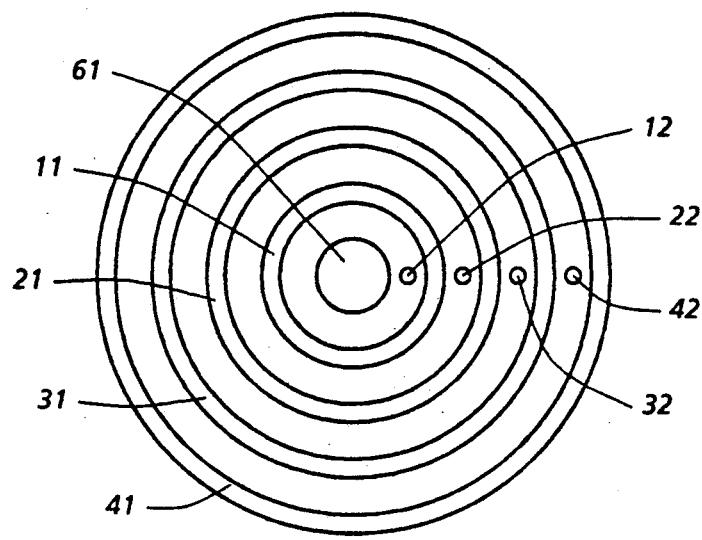
FIG. 3, is a bottom view of the device of FIG. 2 showing a placement of electrical access holes.
Figure 3A:
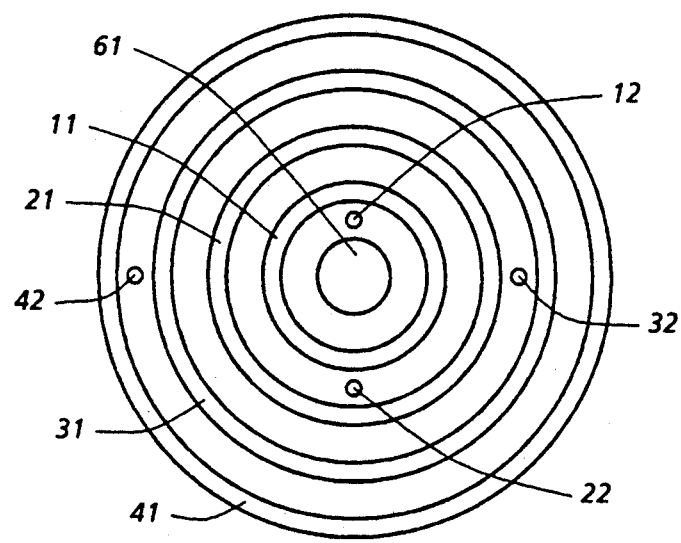
FIG. 3a is an embodiment of the device of FIG. 2 wherein the electrical access holes are placed on different radii.
Figure 3B:
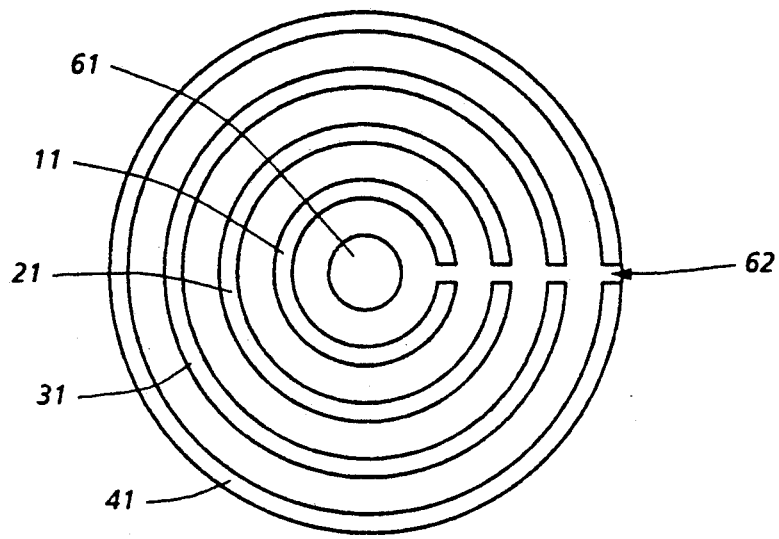
FIG. 3b is a bottom view of an embodiment of the invention of FIG. 2 wherein a radial slot extends axially through the device to allow wiring access.

FIG. 3 is a bottom view of the cylindrical block of ferrite material 60 illustrating the electrical access holes 12, 22, 32 and 42 aligned along a single radial of block 60. A preferred embodiment is illustrated in FIG. 3a wherein electrical access holes 12, 22, 32 and 42 are dispersed on different radial bearings from the center of block 60. A third embodiment depicted in FIG. 3b has a radial slot 62 machined in block 60. The particular method of providing electrical access from the top of block 61 to the bottom where the coils are nested within the channels is not considered critical, and any method of access is considered within the scope of Applicants invention.

Metal shielding, 13, 23, 33 and 43 may cover one or more of the inner surfaces of channels 14, 24, 34 and 44, but must not be in electrical contact with the ferrite block 60. FIG. 2 illustrates this shielding covering one surface of each channel. It is permissible to shield both sides of the channel and/or the bottom, and is a design choice as Applicants' invention will work with, without, or with additional metal shielding between coils 1, 2, 3 and 4. It is also possible to coat the inner surface of channels 14, 24, 34 and 44 by electrodeposition techniques using conductive metals such as gold, silver or copper. Applicants used copper foil on a single surface of the channel, as shown by 13, 23, 33 and 43 in FIG. 2. It is important to note that this shielding should not extend the full 360 degrees around the circumference or it will form a shorted turn with associated losses due to induced currents. If plating or electrodisposition techniques are used, the plated surface should be interrupted to break continuity and preclude continuity 360 degrees around each channel. This additional metal shielding must not make electrical contact with the ferrite.

The lines of flux associated with an eddy current probe form a toroidal shape when an alternating current is passed through the coil (coil is activated). When the probe consists of a coil of wire in a ferrite cup then the inner diameter of the toroidal is determined by the diameter of the center post and the outer diameter is determined by the diameter of the rim of the ferrite cup. Both of these dimensions of the compound probe described herein are controlled, within the constraints imposed by the physical dimensions of the ferrite, by the relative locations of open circuited coil(s), shorted coil(s), and activated coil(s). When inner coil(s) are left open the inner diameter of the toroidal is extended. When a coil (or set of coils) is short circuited and one or more coils are activated by passing an alternating current through them, then secondary currents are induced in the shorted coils. The field associated with these secondary currents serve to shield the flux from the ferrite adjacent to the shorted coils. The losses associated with these secondary currents somewhat reduce the coupling between the probe and the test material. Thus, by shorting unused coils, which generally are those which are further from the center than the activated coil(s), the outside diameter of the toroidal is reduced.

The purpose of shorting the unused coils is to shield the ferrite which extends beyond the outer rim of the activated coil. The flux associated with eddy currents induced in the shorted turns serve to shield this ferrite. Alternatively, the shielding could be provided by counter-wound balancing coils, or by physically covering the unused portions of the ferrite with a shielding material. Shorting the coils is considered to be the preferred embodiment although any method of shielding is considered within the scope of Applicants' invention.

Some examples of individual selected ferrite cup core probe radii are illustrated in FIG. 4-8 and 4a-4b. In FIG. 4, all the coils, 1, 2, 3 and 4 are shown connected in series and activated by a current source supplied by an eddy current instrument or impedance analyzer 70. A switching means (not shown) provides the switching to connect coils 2, 3 and 4 in the various configurations, although not shown in FIG. 4-8.

FIG. 4a shows the resulting flux line pattern comprised of lines of flux 80 when the coils are connected as shown in FIG. 4. This configuration results in the largest radius flux pattern available with the illustrated embodiment.

FIG. 5 shows the coil connections when the compound probe is selected to exhibit the smallest radius cup core probe pattern. Therein, only coil 1 is activated and connected to the current source 70. Coils 2, 3 and 4 are shorted or otherwise inactivated in this configuration. FIG. 5a shows the smallest radius flux field 80 associated with this configuration.

Figure 8:
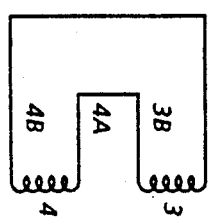
FIG. 8 is another wiring diagram showing another method of wiring the coils to obtain a second variation of the next to smallest radius depicted in FIG. 6.
Figure 8A:
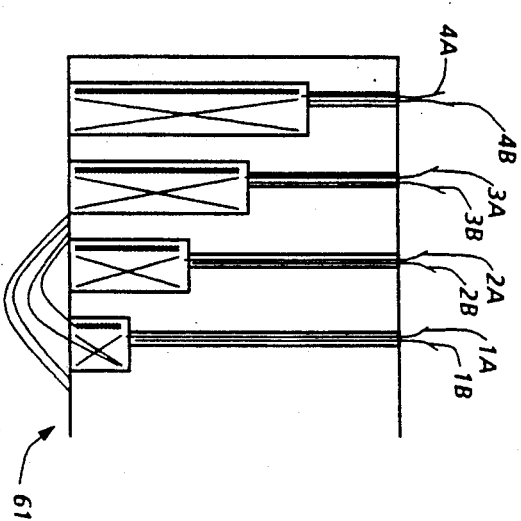
FIG. 8a depicts the flux lines associated with the hookup illustrated in FIG. 8.

FIG. 6 depicts an intermediate sized ferrite cup core configuration wherein coils 1 and 2 are activated and coils 3 and 4 shorted. The flux field 80 shown in FIG. 6a is similar in shape to the flux field illustrated in FIG. 8a. The field in 8a which is generated by activating coil 2, shorting coil 3 and 4 and leaving coil 1 open, is weaker in intensity to the field 80 shown in FIG. 6a.

Figure 7:
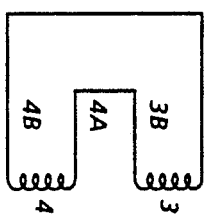
FIG. 7 is a wiring diagram showing a method of wiring the coils to obtain a variation of the next to smallest radius depicted in FIG. 6.
Figure 7A:
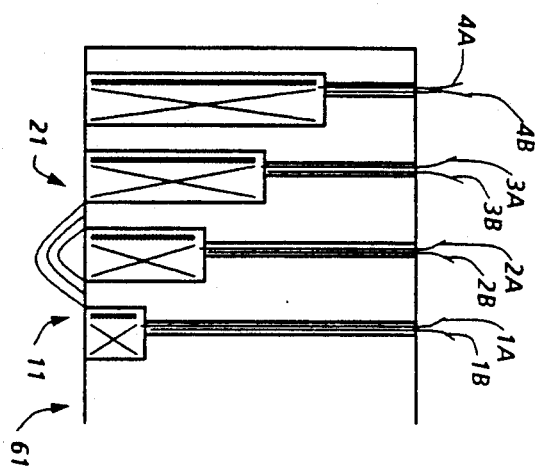
FIG. 7a depicts the flux lines associated with the hookup illustrated in FIG. 7.

When coil 2 is activated and coils 1, 3 and 4 shorted as in FIG. 7, the flux pattern 80 in FIG. 7a has a larger inner diameter, but the same outer diameter as the flux field illustrated in 6a.

There are many other variations and permutations possible than those illustrated in FIGS. 4-8 and those increase as the number of coils increase. It is considered the preferred embodiment to include a switching means (40 in FIG. 1) that can short, open or activated, any coil or combination of coils.

The purpose of this invention is to provide an eddy current probe that offers the advantages of a ferrite cup core probe and also eliminates the requirement to physically change probes when there is a change in the thickness of the material to be interrogated. A compound probe consisting of concentrically nested ferrite cup core probes can be fabricated by selecting a series of commercially available ferrite pot (or cup) cores having a range of diameters such that, with center posts of all but the smallest pot core removed (by sanding, milling, etc.), the cores can be nested with a channel for a coil between the outer diameter of the one core and the inner surface of the rim of the next larger coil. To obtain a "probe" of a particular diameter the coil residing in the channel adjacent to the outer rim having that particular diameter could be connected to the impedance measurement device and the other coils left open or disconnected. However, with this connection scheme, it is as though the activated coil were placed in a ferrite core whose diameter was equal to the diameter of the largest core in the nest. To decrease the diameter to that of the outer rim adjacent to the activated coil, it is necessary to shield the ferrite that lies beyond the rim next to the activated coil.

There are a number of ways to provide this shielding. One effective method is to short all the coils which lie beyond the rim adjacent to the activated coil. Current in the activated coil induces eddy current flow in the shorted turns. The field associated with these induced eddy currents serves to shield the ferrite outside of the desired diameter from the field associated with the activated coil.

This shielding could be provided by mechanically adding a metal foil to cover the ferrite which extends beyond the section of the ferrite which is required to be activated. This approach would be more time consuming than simply changing probes to obtain the necessary size unless the mechanical operations were automated.

The shielding could also be provided by having, in addition to the primary coil in each channel, a counter-wound coil. When an inner coil was activated, the counter-wound coils that reside in channels outside the rim of the activated probe would also be energized thereby providing a cancelling field to shield the ferrite outside the rim of the activated probe.

These variations provide a selectively activated compound ferrite cup core probe that allows many types and sizes of materials to be tested without the nuisance of changing probes.

Obviously, many modifications and variations of the present invention are possible in light of the above teachings. It is, therefore, to be understood that, within the scope of the appended claims, the invention may be practiced otherwise than as specifically described.

What is claimed is:

1. A selectable radii compound ferrite cup core probe for eddy current inspection comprising:
   a block of ferrite containing two or more concentric channels on one surface; and
   two or more concentric coils corresponding to and residing in said concentric channels in said block of ferrite; and
   means for electrical connection of said coils to an impedance measuring device whereby each of said concentric coils may be selectively activated, shorted or left open, such that the compound ferrite cup core exhibits discrete selectable magnetic field inner and outer radii.

2. A selectable radii compound ferrite cup core probe according to claim 1 wherein said block contains 3 concentric channels; and
   said two or more concentric coils number 3.

3. A compound ferrite cup core probe according to claim 1 wherein said block contains 4 concentric channels; and
   said two or more concentric coils number 4.

4. A selectable radii, compound eddy current transducer comprising:
   a block of ferrite material having a first and a second flat surface, wherein two or more channels are machined in the first flat surface;
   two or more coils corresponding to and residing in the channels on the first face of said block;
   means for electrical connection of said two or more coils whereby the effective radii of the magnetic field may be selectively changed by activating select coils while shielding the ferrite which extends beyond the outer rim of the activated probe electronically with a counter-wound coil outside of the outer rim of the activated coil.

5. A selectable radii, compound eddy current transducer comprising:
   a block of ferrite material having a first and a second flat surface, wherein two or more channels are machined in the first flat surface;
   two or more coils corresponding to and residing in the channels on the first face of said block;
   means for electrical connection of said two or more coils whereby the effective radii of the magnetic field may be selectively changed by activating select coils while shielding the ferrite which extends beyond the outer rim of the activated probe electronically by shorting the coils having radii greater than that of the activated coil.

6. A selectable radii, compound eddy current transducer comprising:
   a block of ferrite material having a first and a second flat surface, wherein two or more channels are machined in the first flat surface;
   two or more coils corresponding to and residing in the channels on the first face of said block;
   means for electrical connection of said two or more coils whereby the effective radii of the magnetic field may be selectively changed by activating select coils while shielding the ferrite which extends beyond the outer rim of the activated probe, and wherein the inner radius of the probe is increased by shorting the coils having radii less than that of the activated coil(s).

* * * * *